United States Patent [19]

Vincent et al.

[11] 4,315,031
[45] Feb. 9, 1982

[54] THIOSUBSTITUTED AMINO ACIDS

[75] Inventors: Michel Vincent, Bagneux; Georges Remond, Versailles; Jacques Bure, Neuilly S/Seine, all of France

[73] Assignee: Science Union et Cie, Suresnes, France

[21] Appl. No.: 937,151

[22] Filed: Aug. 28, 1978

[30] Foreign Application Priority Data

Sep. 1, 1977 [GB] United Kingdom ............... 36525/77

[51] Int. Cl.$^3$ .................... A61K 31/24; A61K 31/95; C07C 61/39; C07C 69/753
[52] U.S. Cl. ................................. 424/309; 260/347.2; 546/300; 548/132; 548/144; 548/147; 548/308; 549/65; 560/18; 560/122; 560/125; 562/432; 562/504; 562/507; 564/162; 564/189; 564/191; 424/319; 424/275; 424/305
[58] Field of Search .............. 562/504, 507, 557, 432; 424/319, 305, 309; 560/122, 125, 18

[56] References Cited

U.S. PATENT DOCUMENTS

| 3,347,905 | 10/1967 | Sletzinger et al. | 424/319 |
|---|---|---|---|
| 3,419,655 | 12/1968 | Alburn et al. | 424/319 |
| 3,564,048 | 2/1971 | Fletcher et al. | 424/319 |
| 3,592,812 | 7/1971 | Alburn et al. | 544/30 |
| 3,746,495 | 7/1973 | Malis et al. | 424/319 |
| 3,803,229 | 4/1974 | Alburn et al. | 260/557 R |

OTHER PUBLICATIONS

Coulter, A. W. et al., "Structural and Conformational Analogs of L-Methionine as Inhibitors of Enzymic Synthesis of S-Adenosyl-L-Methionine.", Mol. Pharmacol., (1974), 10(2), 319–334. See Chemical Abstracts vol. 80, (1974), No. 117,621w.
Kirk Othmer, "Encyclopedia of Chemical Technology", 2nd Ed. (1964), vol. 2, p. 157.
Gaitanopoulos, Dimitri E. et al., *J. Medicinal Chemistry,* vol. 19, No. 2, pp. 342–344.
Christensen, Halvor N. et al., *Biochimica et Biophysica Acta,* 469, (1977), pp. 216–220.
Conant, James Bryant, The Chemistry of Organic Compounds, (1947), p. 264, Macmillan, Publ.

*Primary Examiner*—Natalie Trousof
*Assistant Examiner*—Leah Hendriksen
*Attorney, Agent, or Firm*—Gordon W. Hueschen

[57] ABSTRACT

This invention relates to thiosubstituted cyclic amino acids, to a process for their preparation and to pharmaceutical compositions containing them together with an inert non toxic pharmaceutical carrier.

10 Claims, No Drawings

THIOSUBSTITUTED AMINO ACIDS

PRIOR ART

The prior art may be illustrated by the following literature references:

. B 386.257 (CIP of USP 3,803,229) to H. E. Alburn
. Lamar Field & al. J. Med. Chem. (1973) 16 1152

SUMMARY OF THE INVENTION

This invention relates to thiosubstituted cyclic amino acids and more specifically to cyclic amino acids of the formula I

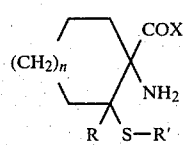

in which
R is a hydrogen atom or a lower alkyl radical,
R' is a hydrogen atom, a lower alkyl radical, a lower alkyl radical which is substituted by an acyloxy, lower alkoxy, lower alkylamino or di(lower alkyl)amino group, an aryl radical, a phenyl-lower alkyl radical, a (substituted phenyl)-methyl radical, a benzhydryl radical or a triphenylmethyl radical,
X is a hydroxy, lower alkoxy, substituted lower alkoxy, (hydroxy)amino, amino or lower alkylamino radical,
and n is 0 or an integer from 1 to 3.

The present invention also provides salts of the compounds of the formula I.

This invention also relates to a process for producing the compounds of the formula I.

The compounds of formula I are endowed with interesting pharmacological properties. They find an use as an immunodepressive agent. They are used in the form of pharmaceutical compositions for the treatment of arthrosis and rheumatic conditions.

PREFERRED EMBODIMENTS

This invention relates to thiosubstituted amino acids, to a process for their preparation and to pharmaceutical compositions containing them.

The present invention provides cycloalkyl amino acids and their derivatives of the formula

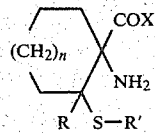

in which R is a hydrogen atom or a lower alkyl radical,
R' is a hydrogen atom, a lower alkyl radical, a lower alkyl radical which is substituted by an acyloxy, lower alkoxy, lower alkylamino or di(lower alkyl)amino group, an aryl radical, a phenyl-lower alkyl radical, a (substituted phenyl)-methyl radical, a benzhydryl radical or a triphenylmethyl radical,
X is a hydroxy, lower alkoxy, substituted lower alkoxy, (hydroxy)amino, amino or lower alkylamino radical,
and n is 0 or an integer from 1 to 3.

The present invention also provides salts of the compounds of the formula I. When X is a hydroxy radical, the compounds are amphoteric and give salts with both mineral or organic acids and inorganic or organic bases. When X is a lower alkoxy, amino, or lower alkylamino radical, only acid addition salts may be formed.

When X is a hydroxyamino radical, acid addition salts and also salts with strong bases may be formed.

The compounds of the formula I include two asymmetric carbon atoms and consequently may be resolved into the cis and trans geometric isomers. The resulting cis and trans isomers may be further resolved into the dextro- and laevo-rotatory optical isomers.

Among the compounds of the formula I, there may be mentioned the following:

(a) compounds of the formula

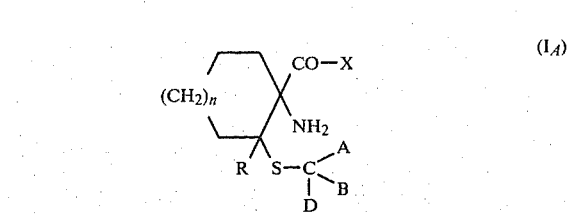

in which R, X and n have the meanings given above, each of A and B is a hydrogen atom or a lower alkyl, hydroxy lower alkyl, amino lower alkyl, lower alkoxy-lower alkyl, lower alkylthio-lower alkyl or phenyl radical, and
D is a hydrogen atom or, when A and B are both phenyl radicals, a phenyl radical;

(b) compounds of the formula

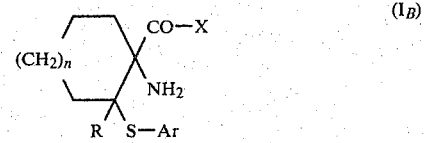

in which X, R and n have the meanings given above and
Ar is an unsubstituted or monosubstituted phenyl, thienyl, furyl, thiazolyl, oxadiazolyl or pyridyl radical;

(c) compounds of the formula

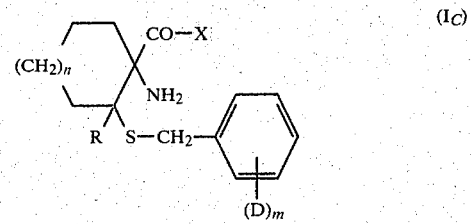

in which R, X and n have the meanings given above,
the or each D is a halogen atom or a lower alkoxy, trifluoromethyl, amino, lower alkylamino or lower acylamino radical, and
m is zero or an integer from 1 to 3; and (d) compounds of the formula

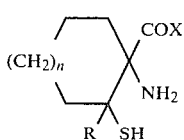

in which X, R and n have the meanings given above.

With the carbonyl group, the substituent X may form a carboxy group when X is a hydroxy radical, lower alkyl and substituted lower alkyl esters thereof when X is a lower alkoxy radical, the amides thereof when X is an amino or lower alkylamino radical and the hydroxamates thereof when X is a hydroxyamino radical.

The compounds of the formula (I) are derivatives of cyclopentane when n is zero, derivatives of cyclohexane when n is 1, derivatives of cycloheptane when n is 2 and derivatives of cyclooctane when n is 3.

Those compounds in which n is zero or 1 are preferred.

When Ar is a substituted phenyl, the benzenic ring is substituted with one to three substituents selected from halogen atoms, a lower alkoxy, a trifluoromethyl radical, a lower alkylthio, a lower alkylenedioxy, a hydroxy and a lower alkyl radical.

By the term "lower" alkyl radical there is meant an alkyl radical having from 1 to 6 carbon atoms in straight or branched chain.

Examples of lower alkyl radicals are the methyl, ethyl, isopropyl, secbutyl, neopentyl, tertbutyl, and n-hexyl radicals.

The compounds of the formula (I) and the salts thereof possess interesting pharmacological properties, especially immunodepressive properties. They exert a favourable effect on the tensile strength of the derm and a protective effect on soluble collagen.

These properties may be illustrated in mice (strain CBA), where they show a significant decrease in the delayed contact hypersensitivity to oxazolone in vivo.

The compounds of the formula (I) and the salts thereof therefore find use in human and veterinary medicine as immuno-depressive agents in the treatment of rheumatic fever and conditions associated with proteic hypersecretion.

They may also be used as antibacterial agents either alone or in association with antibacterial phenylsulphamide derivatives such as sulfametoxazole or sulfapyridazine.

In addition, they may be used as immunodepressive agents in organ transplants such as heart transplants, liver transplants and kidney transplants.

The present invention provides pharmaceutical compositions comprising as active ingredient at least one compound of the formula (I) as geometric or optically-active isomer thereof of a physiologically tolerable salt thereof, in admixture or conjunction with a pharmaceutically suitable carrier.

The pharmaceutical compositions according to the invention may be in a form suitable for oral, parenteral, rectal, or sublingual administration, for example in the form of tablets, coated tablets, soft gelatine capsules, dragees, cachets, pills, drops, drinkable suspensions or solutions, injectable solutions or suspensions packed in ampouls, phials, multidose flasks or self-injectable syringes, suppositories and sublingual tablets.

The pharmaceutical compositions may also incorporate binders, fillers, adsorbent coatings which preserve the active ingredient from digestive, enzymatic degradation, buffering agents, and/or agents which increase or decrease the availability of the active ingredient in the body.

As carriers or diluents there may be used, for example talc, starches, zein, magnesium stearate, magnesium phosphate, methyl cellulose and hydroxylpropyl cellulose for dry compositions; water and saline solutions for liquid compositions; and cocoa butter and polyethyleneglycol stearates for suppositories.

Usually the dosage regimen will vary depending on the age and the weight of the patient, the illness to be treated and the severity of the illness. In man, the daily doses may range from 100 mg to 2 mg and the unit dosage may range from 100 to 400 mg depending on the method of administration.

The present invention also provides a process for preparing compounds of the formula (I) which comprises submitting a cycloalkanone of the formula

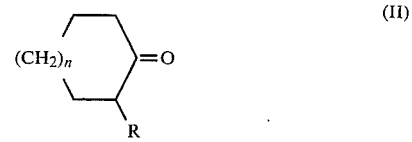

in which R and n have the meanings given above
to the action of a halogenating agent to produce an α-halocycloalkanone of the formula

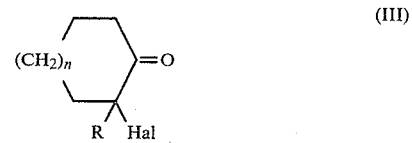

in which Hal is a chlorine or bromine atom,
reacting the latter with benzylthiol to produce an S-benzylthio derivative of the formula

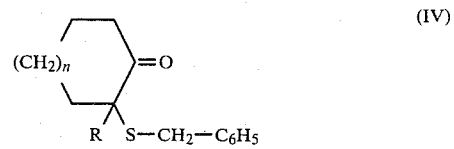

reacting this compound with an alkali metal cyanide and ammonium carbonate to produce the corresponding hydantoin of the formula

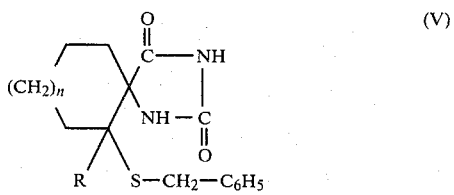

hydrolysing this compound with a mild alkali to produce
an amino-acid of the formula

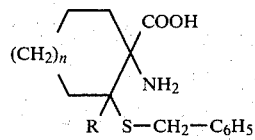

and, if desired, debenzylating the latter under reductive conditions to produce the corresponding thiol of the formula

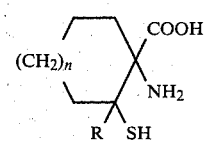

The thiol derivatives of the formula (VII) may then be alkylated, arylated or arylalkylated with an alkylating agent, an arylating agent or an arylalkylating agent under appropriate conditions to produce a compound of the formula

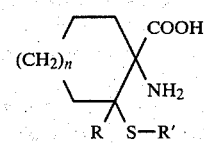

in which R′ is a lower alkyl, substituted lower alkyl, aryl, phenyl-lower alkyl, substituted phenylmethyl, benzhydryl or triphenylmethyl radical.

The compounds of the formulae (VI), (VII) and (VIII) may also be converted into the corresponding lower alkyl esters, amides, substituted amides or hydroxamates, preferably after blocking the free amino group with a trityl radical, by condensing the carboxy group with a lower alkanol, an amine or hydroxylamine in the presence of a dehydrating agent or by forming previously a functional derivative of the carboxy group.

It may also be convenient to prepare first a lower alkyl ester, such as the methyl or the isopropyl ester, and to convert it into a substituted lower alkyl ester by transesterification or into an amide or a lower alkylamide by transamidation. The hydroxyamates may also be produced by converting the lower alkyl esters into a hydroxamate by heating the ester with hydroxylamine or salt thereof.

Resolution may be carried out on the compounds of the formula (VI), (VII) or (VIII). It may also be performed at a previous step, such as on compounds of the formula (V).

Resolution of the optically-inactive compounds into the cis or trans geometrical isomers is preferably carried out using an optically active reagent such as an optically active base, for example ephedrine, brucine, strychnine or d-threo 2-dimethylamino-1-p-nitrophenyl-1,3-propanediol or by using an optically-active acid, for example d-dibenzoyltartaric acid, dimethyl tartramic acid or d-camphanic acid.

Resolution into the optically-active laevo and dextro isomers may be carried out using a chiral reagent, such as Mosher reagent.

Salification of the compounds of the formula (I) is carried out either by adding a mineral or organic acid, for example hydrochloric acid, hydrobromic acid, sulphuric acid, nitric acid, phosphoric acid, formic acid, butyric acid, benzoic acid, nicotinic acid and glycyrretic acid, or by adding an inorganic or organic base, for example sodium hydroxide, potassium hydroxide, lithium hydroxide, magnesium hydroxide, strontium hydroxide and ferrous hydroxide; a lower alkylamine such as methylamine or diethylamine, on amino-lower alkanol such as diethanolamine, a phenyl-lower alkylamine such as phenyl methylamine or a phenyl-lower alkylamine such as phenethylamine, a pyridyl base such as β-pyridyl methylamine or an arylamine such as naphthylamine or dinaphthylethylenediamine.

In the process of the present invention, the following features are preferred:

(1) halogenation of the cycloalkanone of the formula (II) is carried out with a halogenating agent such as a halogen, for example chlorine or bromine, a N-haloalkyl or -arylamide for example N-chlorosuccinimide, N-bromoacetamide, N-bromobenzamide, N-bromophtalimide, 5,5-dichlorodiphenylhydantoin, thionyl chloride, sulfuryl chloride, a lower alkyl hypochlorite, for example tertbutyl hypochlorite or a pyridinium perhalogenide, for example pyridinium perbromide;

(2) halogenation is carried out in an inert solvent, preferably a polar solvent, for example dioxan, pyridine, dimethylacetamide, hexamethylphosphoramide or acetic acid;

(3) condensation between the α-haloketone of the formula (III) and the benzylmercaptan is carried out either in a basic medium or by previously converting the benzyl mercaptan into an alkali metal salt, such as the sodium, potassium or lithium mercaptide;

(4) condensation between the α-benzylthioketone of the formula (IV) and an alkali metal cyanide is carried out under the conditions of the Strecker reaction using ammonium carbonate as the source of ammonia;

(5) hydrolysis of the hydantoin of the formula (V) is carried out using a mild alkaline agent such as sodium carbonate, lithium carbonate or barium hydroxide; it may be convenient to carry out the condensation and the hydrolysis in one step without isolating the intermediate hydantoin;

(6) debenzylation of the α-benzylthio-amino-acid of the formula (VI) is carried out by hydrogenolysis or by the action of an alkali metal in ammonia such as sodium, potassium, lithium or calcium;

(7) alkylation of the α-thio-amino acid of the formula (VII) is carried out using an alkylating agent such as a lower alkyl halide in a basic medium, a lower alkyl sulphate in a basic medium, or an alkylene oxide, for example ethylene oxide; when an alkylene oxide is used, the resulting hydroxy alkyl derivative may be further converted into an alkyl ether, or into an ester with an acylating agent or into an aryl or alkyl sulphonyl ester. The latter may be further converted into an amine or a lower alkylamino derivative by functional exchange;

(8) the arylation of the α-thio derivative of the formula (VII) is carried out using an arylating agent such as a bromo or iodo derivative, in a polar medium such as pyridine or dimethyl formamide;

(9) arylalkylation of the α-thio derivative of the formula (VII) is carried out using an arylalkyl halide in the presence of a proton acceptor such as a tri(lower alkyl)amine, an aryl di(lower alkyl)amine, a pyridine base, a di(lower alkyl)alkyl carboxamide or a basic reagent such as an alkali metal or alkaline earth metal carbonate, phosphate or hydroxide; examples of such reagents are triethylamine, dimethylaniline, pyridine, collidine, dimethylacetamide, sodium carbonate, calcium carbonate, magnesium phosphate and magnesium hydroxide.

The present invention also provides as new compounds the following intermediate compounds:

(1) the α-haloketones of the formula

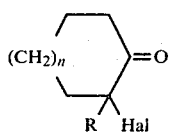
(III)

in which Hal is a chlorine or bromine atom and R and n have the meanings given above;

(2) the benzylthio-cycloalkanones of the formula

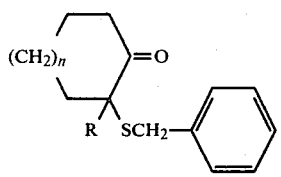
(IV)

in which R and n have the meanings given above; and (3) the hydantoins of the formula

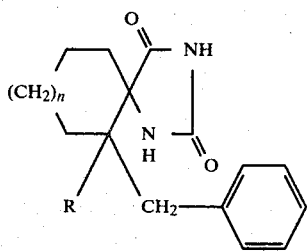
(V)

in which R and n have the meanings given above.

The following Examples illustrate the invention. The temperatures are expressed in degrees Centigrade.

EXAMPLE I dl 1-amino-2-methyl-2-benzylthio cyclohexane carboxylic acid (mixture of α and β isomers)

Step A 2-methyl-2-chlorocyclohexanone 112 g of 2-methylcyclohexanone and 500 ml carbon tetrachloride are mixed in a three neck flask and 90 ml of thionyl chloride in 150 ml of carbon tetrachloride are added dropwise in the course of 60 minutes, under vigorous stirring while keeping the temperature at about 15° with a water bath. Stirring is maintained for a further 2 hours. The reaction medium is then washed three times with dilute hydrochloric acid, twice with a saturated solution of sodium bicarbonate and finally with a saturated solution of sodium chloride. The organic phase is separated, dried over sodium sulphate and the solvent is evaporated off under reduced pressure. The dry residue of 2-methyl-2-chlorocyclohexanone weighing about 180 g is purified by fractional distillation. The main fraction boils at 85°–90° (20 mm Hg); $n_D^{25} = 1.4672$.

Step B 2-methyl-2-benzylthiocyclohexanone 36.5 g of 2-methyl-2-chlorocyclohexane are dissolved in 70 ml ethanol. To this solution is added a mixture of 82 g benzylmercaptan 26.4 g of sodium hydroxide and 330 ml ethanol and the whole is heated to reflux. A pink colour appears after 15 minutes and the mixture is then allowed to cool to room temperature and the solvent is distilled off. The oily residue is taken up in 400 ml water and the resulting suspension is extracted with methylene chloride. The organic phases are united, washed with water until neutral, dried over sodium sulphate and the solvent is evaporated off. The residue is purified by fractional distillation. 120 g of 2-methyl-2-benzylthiocyclohexanone are recovered, boiling at 142°–144° (yield=78%).

Step C 2-methyl-2-benzylthiocyclohexyl-spiro-hydantoine.

Into a closed 250 ml vessel heated in a water-bath at about 50° there are successively introduced 2.5 g of potassium cyanide in 15 ml water then a mixture of 11.7 g of 2-methyl-2-benzylthiocyclohexanone, 9.6 g ammonium carbonate and 40 ml 60% ethanol.

The addition takes about 15 minutes and the whole mixture is allowed to stand at the same temperature for 45 hours while stirring. The reaction mixture is evaporated to dryness. The dry residue is taken up in 180 ml water and 100 ml ether. After vigorous stirring, the precipitate is isolated by filtration, washed with water and dried. 2.5 g of hydantoin are recovered, melting at 210°. A second crop is obtained, by crystallization from the mother-liquor, weighing 0.9 g.

The total yield amounts to about 20%.

Step D 2-methyl-2-benzylthio-1-aminocyclohexyl-1-carboxylic acid.

63.1 g of baryta are dissolved by heating in 500 ml water and the solution is filtered. The filtrate is added to a suspension of 30.5 g of the spirohydantoin of step C in 150 ml water. To the mixture, water is added until a total volume of 1000 ml is obtained. The solution is transferred into a closed vessel and heated to 140° while stirring for 65 hours. The temperature is allowed to drop to 90° and the remaining liquid is introduced into a flask. The walls of the vessel are twice washed with N hydrochloric acid and the acid solutions are added to the reaction mixture. This solution is rendered acidic by adding hydrochloric acid to pH 1.

The solution is then neutralized with sodium bicarbonate to pH 6.3. A precipitate appears and the suspension is kept in a refrigerator. The walls of the vessel are then washed with hot chloroform and the chloroformic solution is filtered and evaporated to dryness. The dry residue is ground with a few ml of ether. The crystalline mixture is filtered. The insoluble matter is dried and then taken up in N hydrochloric acid. This solution is chromatographed on a column charged with Dowex $XW_8$. Elution is carried out with triethylamine until the eluates do not react with ninhydrin.

After evaporation under reduced pressure, 7 g of 2-benzylthio-2-methyl-1-aminocyclohexyl-1-carboxylic acid are recovered. The melting point is 215°. The yield amounts to about 25%.

| Analysis: $C_{15}H_{21}NO_2S = 279.40$ | | | | |
|---|---|---|---|---|
| | C | H | N | S % |
| Calculated | 64.48 | 7.57 | 5.01 | 11.47 |
| Found (after 1 hour at 150°) | 64.20 | 7.20 | 5.00 | 11.32 |

This compound retains very strongly some water.

The infra-red spectrum is in accordance with the structure, but without specific stretchings.

NMR spectrum: in accordance with the structure the integration of the fields is correct.

EXAMPLE II dl 1-amino-2-benzylthiocyclohexyl-1-carboxylic acid

Using the procedure described in Example I, the following compounds have been obtained from cyclohexanone:

2-benzylthiocyclohexanone, BP 128°–132°/0.07 mm Hg (yield 72%);

2-benzylthiocyclohexyl-1-spirohydantoin, MP 216°;

dl 1-amino-2-benzylthiocyclohexyl-1-carboxylic acid, MP 220° (from water);

| Analysis: $C_{14}H_{19}NO_2S = 265.377$ | | | | |
|---|---|---|---|---|
| | C | H | N | S % |
| Calculated | 63.40 | 7.35 | 5.29 | 12.09 |
| Found | 62.93 | 7.03 | 5.22 | 11.92 |

This compound is soluble in dilute hydrochloric acid. After evaporation of the solvent the hydrochloride is obtained.

EXAMPLE III dl 1-amino-2-thiocyclohexyl-1-carboxylic acid 100 ml of liquid ammonia are condensed in a mixture of solid carbon dioxide and acetone. The liquid is allowed to warm to about $-30°$ then 6 g 1-amino-2-benzylthiocyclohexyl-1-carboxylic acid of example II is added thereto and 3.2 g sodium until a persistent blue color allowed to stand for one hour while stirring and the reaction mixture remains blue during this period. The excess of reagent is destroyed by cautious addition of ammonium chloride and ammonia is evaporated off at room temperature. The solvent is evaporated off under reduced pressure. The dry residue is taken up in water. The suspension is rendered slightly acidic by adding hydrochloric acid to pH2. The solution is evaporated off. The residue is washed with acetone then taken up in 200 ml isopropanol. The residue from evaporation weighs about 3 g. It is still not free from mineral salts. It is converted for purification into its hydrochloride. The hydrochloride melts over 250°. S%=13,98 (th.14,20)

RMN spectrum (D$_2$O): unresolved signals from 2.6 to 3.1 ppm (one proton); signals from 1.6 to 2.6 ppm (10 protons of which 2 are singulet).

The pure product was obtained through HPL chromatography on a column filled with silica (silica RP8 Merck 25–40μ)

| Analysis: $C_7H_{13}CL\ NO_2S . \frac{1}{2}H_2O = 220.72$ | | | | |
|---|---|---|---|---|
| | C | H | N | Cl | S % |
| Calculated | 38.09 | 6.85 | 6.34 | 16.06 | 14.52 |

| | C | H | N | Cl | S % |
|---|---|---|---|---|---|
| Found | 38.14 | 6.37 | 6.34 | 16.42 | 14.35 |

The hydrochloride is soluble in water. The pH of the aqueous solution is about 3.5.

EXAMPLE IV dl 1-amino-2-(p-chlorophenylthio)-cyclohexyl-1-carboxylic acid.

Using the procedure described in Example I the title compound is obtained. It melts above 250° C. (with dec)

| Analysis: $C_{13}H_{16}Cl\ NO_2S = 285.8$ | | | | |
|---|---|---|---|---|
| | C | H | N | Cl | S |
| Calculated | 54.64 | 5.64 | 4.90 | 12.41 | 11.22 |
| Found | 54.26 | 5.49 | 4.89 | 12.50 | 11.40 |

EXAMPLE V dl 1-amino-2-benzylthiocyclopentyl-1-carboxylic acid

Using the procedure described in Example I, the title compound is obtained as the mono-hydrate. The melting point of the hydrate cannot be determined accurately.

The compound is soluble in dilute methanesulphonic acid by heating to about 40°. After evaporation of the solvent, the methane sulphonate is isolated.

| Analysis: $C_{13}H_{17}O_2\ N\ S\ .\ H_2O$ | | | | |
|---|---|---|---|---|
| | C | H | N | S % |
| Calculated | 57.97 | 7.10 | 5.20 | 11.90 |
| Found | 58.69 | 7.05 | 5.20 | 12.46 |

EXAMPLE VI dl 2-methyl-2-benzylthio-1-aminocyclopentyl-1-carboxylic acid

The starting material, 2-methylcyclopentanone, is obtained from ethyl 2-oxocyclopentyl-1-carboxylate by methylation using methyl iodide and sodium hydride as the methylating agent.

The title compound is obtained from 2-methyl cyclopentanone using the procedure described in Example I. It melts above 250° (with dec.).

This compound is soluble in dilute aqueous hydrochloric acid but insoluble in aqueous alkali metal hydroxides.

| Analysis: $C_{14}H_{19}NO_2S = 265.38$ | | | |
|---|---|---|---|
| | C | H | N |
| Calculated | 63.36 | 7.22 | 5.28 |
| Found | 63.34 | 7.07 | 5.48 |

Similarly, from ethyl 2-oxocyclopentyl or cyclohexyl-1-carboxylate and the corresponding alkylating agents, 2-ethyl and 2-isopropyl and 2-butylcyclopentanones or hexanones are obtained providing the necessary starting materials for the desired 1-amino-2-lower alkylthiocyclopentyl or cyclohexyl-1-carboxylic acid.

EXAMPLE VII dl 1-amino-2-thienylthio-cyclohexyl-1-carboxylic acid

Using the procedure described in Example I and starting from 2-chlorocyclohexane and (thienyl-2)-thiol, the title compound is obtained as a mixture of diastereo-isomers.

It melts above 250°. It is fairly soluble in the stoichiometric amount of potassium hydroxide.

| Analysis: $C_{11}H_{15}NO_2S_2 = 257.378$ | | | | |
|---|---|---|---|---|
| | C | H | N | S % |
| Calculated | 51.33 | 5.87 | 5.44 | 24.91 |
| Found | 51.42 | 6.04 | 5.70 | 24.81 |

EXAMPLE VIII dl 1-amino-2-thiocyclopentyl-1-carboxylic acid 900 ml liquid ammonia are condensed in acetone at 70° C. To it 20 g of 1-amino 2-benzylthio cyclopentyl carboxylic acid are added at once then portionwise about 8 g of sodium cuttings. The mixture takes a deep blue colour. After one hour standing, the mixture is discolourized by adding ammonium chloride and ammonia is let to evaporate off at ambient temperature. The residue is taken up in water then added to hydrochloric acid until the pH. value reaches 2. The product is passed through a column filled with a polycarboxylic resin sold under the trade Name Dowex 50 W8 previously treated with hydrochloric acid then water.

The column is washed with water and eluted by passing an aqueous solution of triethylamine (50 g/l). The eluate is divided in 16 fractions of 25 ml each. The thiol derivative is found in the fractions 9 to 16. They are evaporated off, the the residue is washed with ether then ethanol-4.3 g of dl 1-amino 2-thiocyclopentyl 1-carboxylic acid are obtained i.e. a yield of 27%.

It is soluble in water (c>0,5 mole/l). The pH of the aqueous solution is 6.4.

| Analysis: $C_6H_{11}NO_2S = 161.32$ | | | | |
|---|---|---|---|---|
| | C | H | N | S % |
| Calculated | 44.67 | 6.87 | 8.68 | 19.87 |
| Found | 44.52 | 7.02 | 8.55 | 19.59 |

By blocking both the amino and the thio groups by tritylation using triphenylmethyl chloride, this acid may be esterified

EXAMPLE IX

Separation of the two diastereo isomers of 2-benzylthio 1-amino cyclopentyl 1-carboxylic acid 3.5 g of dl 2-benzylthio 1-amino cyclopentyl 1-carboxylic acid in a mixture of chloroform-methanol are injected through a high pressure chromatograph fitted with a column filled with 1.5 kg silica (10–40μ) suspended in cyclohexanone.

The two diastereo isomers are successively eluted. They are still contamined with mineral salts.

After further purification by high pressure liquid chromatography on a column fitted with silica (5–20μ) RP8 the compounds are eluted with methanol. The two diastereo isomers are crystallized from a mixture of chloroform-methanol-ethyl ether.

The first isomer is obtained in two crops weighing a total of 2 g (-isomer α).

The second isomer is obtained in two crops weighing 0.9 g (-isomer β).

| Isomer α | | | | |
|---|---|---|---|---|
| Melting point > 250° C. | | | | |
| soluble in N/10 aqueous solution of methane sulfonic acid | | | | |
| Analysis: $C_{13}H_{17}NO_2S = 251.35 + 2.5\%$ water | | | | |
| | C | H | N | S % |
| Calculated | 62.12 | 6.82 | 5.67 | 12.76 |
| Found | 62.00 | 6.72 | 5.68 | 13.18 |
| Isomer β | | | | |
| Melting point > 250° C. | | | | |
| Analysis: $C_{13}H_{17}NO_2S = 251.35$ | | | | |
| | C | H | N | S % |
| Calculated | 62.12 | 6.82 | 5.57 | 12.76 |
| Found | 62.01 | 7.17 | 5.60 | 12.73 |

EXAMPLE X

Separation of the two diastereo isomers of dl 1-amino 2-methyl 2-benzylthio cyclohexyl 1-carboxylic acid.

The two diastereo isomers are separated by a high pressure liquid chromatograph (Apparatus Jobin Yvon) fitted with a column filled with 1.5 kg silica (10–40μ) suspended in cyclohexanone.

A solution of 3 g of the dl compound in 100 ml of a mixture of chloroform/methanol is injected. The two diastereo-isomers are successively recovered and the solvents are evaporated off.

The first isomer is obtained in two crops (total weight 1.87 g). The second isomer is obtained by crystallization and from the mother liquors (total weight 0.4 g). The ratio of the diastereoisomers in the dl mixture is about 75 isomer α/ about 25 isomer β.

| Isomer α | | | | |
|---|---|---|---|---|
| Melting point 262° (with dec.) | | | | |
| soluble in 10ml N/10 sodium hydroxide | | | | |
| Analysis: $C_{15}H_{21}NO_2S = 279.40$ | | | | |
| | C | H | N | S % |
| Calculated | 64.48 | 7.58 | 5.01 | 11.48 |
| Found | 64.39 | 7.39 | 5.14 | 11.82 |
| Isomer β | | | | |
| Melting point 260° (with dec.) | | | | |
| soluble in N/10 sodium hydroxide | | | | |
| Analysis: $C_{15}H_{21}NO_2S = 279.40$ | | | | |
| | C | H | N | S % |
| Calculated | 64.48 | 7.58 | 5.01 | 11.48 |
| Found | 64.39 | 7.41 | 5.15 | 11.62 |

EXAMPLE XI

Separation of the diastereoisomers of 2-p.chlorophenylthio 1-amino cyclohexyl 1-carboxylic acid.

Using the same procedure as in example IX and starting from 5 g (dl 2-p.chlorophenylthio 1-amino cyclohexyl 1-carboxylic acid, 3 g of a diastereoisomer are obtained (isomer α). From the liquors are recovered 1 g of the α-isomer, still impure, and 0.5 g of a mixture containing the second diastereoisomer contaminated with mineral salts.

The diastereoisomer α melts over 250° (with dec.). Its hydrochloride is freely soluble in water.

| Analysis for the hydrochloride: $C_{13}H_{16}ClNO_2S$, $ClH = 322.27$ | | | | | |
|---|---|---|---|---|---|
| | C | H | N | S | Cl total | Cl ionic |
| Calculated | 48.45 | 5.32 | 4.35 | 9.95 | 22.00 | 11.00 |
| Found | 48.30 | 5.37 | 4.67 | 9.91 | 22.65 | 11.45 |

EXAMPLE XII

Pharmacological testing of the compounds of formula I

The compounds of formula I have been tested in comparison with d-penicillamine, on the polymerisation of collagen according to the technique described by Jaffe and Nimmi.

In a similar fashion the immunodepressive action of the compounds of formula I has been determined in comparison with that of d-penicillamine, methotrexate, endoxan and azathioprine.

Immunodepressive Effect

The compounds have been tested according to the procedure described in the test of cultaneous delayed hypersensivity with oxazolone (Phanuphak and coll. J. of Immunol. 1974, 112).

The mice are rendered sensitive through applications on the back with a solution at 3% of oxazolone in a mixture of acetone and olive oil. The challenge is performed 5 days later by spraying on the ear with a 3% solution of oxazolone. The hypersensitivity reaction is evaluated 24 and 48 hours after the spraying. The depth of the infiltration is determined and the number of animals which minimally respond to this test is noticed. The compounds are administered either three times, once two days before and on the day of sensibilization, or once, two days after the sensibilization.

Methotrexate is administered at the doses of 20 and 40 mg/kg IP. Endoxan is administered at doses from 50 to 200 mg/kg intraperitoneously, whereas azathioprine is administered intraperitoneously at the doses of 100 and 300 mg/kg.

The compounds of formula I are administered orally at doses ranging from 50 to 200 mg/kg. At a dose of 100 mg/kg, about half of the treated mice respond to the delayed hypersensitivity test.

Acute Toxicity

The acute toxicity of the compounds of formula I has been determined on batches of mice (strain CD) weighing about 20 g. The compounds are administered orally at increasing doses.

The animals are kept under survey for 8 days. The deaths, if any, are numbered.

The average lethal dosis ($LD_{50}$) are graphically determined. They range from 1 g to more than 2 g/kg.

In the same fashion the $LD_{50}$ for methotrexate is 0.15, that of endoxan is about 1 g, and that of azathioprine is about 2 g/kg.

EXAMPLE XIII 1-amino 2-methylthio 2-methyl cyclohexyl 1-carboxylic acid (mixture of diastereoisomers)

Starting with dl 1-amino 2-thio 2-methyl cyclohexyl 1-carboxylic acid, obtained by debenzylating dl 1-amino 2-benzylthio 2-methyl cyclohexyl 1-carboxylic acid with sodium in liquid ammonia, and reacting it with triphenylmethyl chloride in dioxane, 1-triphenylmethylamino 2-thio 2-methyl cyclohexyl 1-carboxylic acid is produced. It is further reacted with dimethyl sulphate in strong basic medium to obtain 1-triphenylmethylamino 2-methylthio 2-methyl cyclohexyl 1-carboxylic acid. The tritylamino derivative is finally hydrolysed in aqueous acetic acid and 1-amino 2-methylthio 2-methyl cyclohexyl 1-carboxylic acid is recovered as colourless crystals.

The compounds sublimates over 225° without melting. It is very soluble in water.

| Analysis: $C_9H_{17}NO_2S = 203.31$ | | | |
|---|---|---|---|
| C | H | N | S % |
| Calculated 53.17 | 8.43 | 6.89 | 15.77 |
| Found 53.24 | 8.59 | 6.97 | 15.93 |

EXAMPLE XIV

Tablets containing 250 mg of 2-methyl 2-benzylthio 1-amino cyclohexyl 1-carboxylic acid per dosage unit.

| | |
|---|---|
| active ingredient | 2.5 kg |
| maize starch | .250 |
| corn starch | .250 |
| ethyl cellulose | .04 |
| magnesium silicate | .150 |
| talc | .100 |
| formolated casein | .025 |
| lactose | .200 |

For 10,000 tablets weighing each 0.350 g.

What we claim is:

1. A cycloalkyl amino acid or ester of the formula

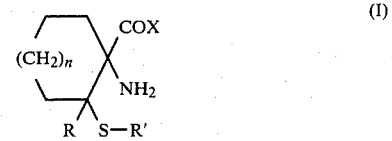

in which

R is hydrogen or lower alkyl;

R' is halophenyl, phenyl, phenyl-lower alkyl or halophenylmethyl;

X is hydroxy or lower alkoxy; and, n is 0 or an integer from 1 to 3, inclusive.

2. The salts of the compounds of claim 1 with mineral or organic acids and inorganic or organic bases.

3. A compound according to claim 1 which is 2-benzylthio 1-amino cyclopentyl carboxylic acid and its diastereoisomers.

4. A compound according to claim 1 which is 2-(p.chlorophenylthio) 1-amino cyclohexyl carboxylic acid and its diastereoisomers.

5. A compound according to claim 1 which is 2-methyl 2-benzylthio 1-amino cyclohexyl 1-carboxylic acid and its diastereoisomers.

6. A compound according to claim 1 which is 2-benzylthio 1-amino cyclohexyl 1-carboxylic acid and its diastereoisomers.

7. A pharmaceutical composition useful as an immunodepressive agent containing as active ingredient an effective amount of at least one compound of claim 1 or a salt thereof, together with an inert non-toxic pharmaceutically-acceptable excipient or vehicle.

8. A pharmaceutical composition according to claim 17 in which the unit dosage ranges from 100 to 400 mg of a compound of claim 1 or a salt thereof.

9. A method for a treating hypersensitivity reaction in a patient which consists in administering to said patients a small but effective amount of a compound of claim 1 or a salt thereof with a mineral or organic acid or a salt thereof with a mineral or organic base.

10. The method of treatment of claim 9 wherein the small but effective amount of a compound of claim 1 ranges from 100 mg to 2 g per day.

* * * * *